US012629336B2

(12) United States Patent
Barrows

(10) Patent No.: US 12,629,336 B2
(45) Date of Patent: May 19, 2026

(54) COMPOSITIONS AND METHODS OF USE THEREOF FOR TREATMENT OF MASTITIS

(71) Applicant: CureMast, Inc., Atlanta, GA (US)

(72) Inventor: Thomas Harry Barrows, Austell, GA (US)

(73) Assignee: CureMast, Inc., Atlanta, GA (US)

( * ) Notice: Subject to any disclaimer, the term of this patent is extended or adjusted under 35 U.S.C. 154(b) by 556 days.

(21) Appl. No.: 17/796,599

(22) PCT Filed: Feb. 2, 2021

(86) PCT No.: PCT/US2021/016165

§ 371 (c)(1),
(2) Date: Jul. 29, 2022

(87) PCT Pub. No.: WO2021/158517

PCT Pub. Date: Aug. 12, 2021

(65) Prior Publication Data

US 2023/0057782 A1 Feb. 23, 2023

Related U.S. Application Data

(60) Provisional application No. 62/969,419, filed on Feb. 3, 2020.

(51) Int. Cl.

| | |
|---|---|
| *A61K 9/1274* | (2025.01) |
| *A61K 31/198* | (2006.01) |
| *A61K 31/722* | (2006.01) |
| *A61K 31/785* | (2006.01) |
| *A61K 45/06* | (2006.01) |
| *A61K 47/14* | (2017.01) |

(52) U.S. Cl.
CPC .......... *A61K 9/1274* (2013.01); *A61K 31/198* (2013.01); *A61K 31/722* (2013.01); *A61K 31/785* (2013.01); *A61K 45/06* (2013.01); *A61K 47/14* (2013.01)

(58) Field of Classification Search
CPC .. A61K 9/1274; A61K 31/198; A61K 31/722; A61K 31/785; A61K 45/06; A61K 47/14
See application file for complete search history.

(56) References Cited

U.S. PATENT DOCUMENTS

| | | | | |
|---|---|---|---|---|
| 3,636,194 A | * | 1/1972 | Parizeau | A61K 31/43 514/192 |
| 5,262,164 A | | 11/1993 | Damani | |
| 5,531,925 A | | 7/1996 | Landh | |
| 2004/0229813 A1 | | 11/2004 | DiPiano | |
| 2009/0004122 A1 | * | 1/2009 | Modak | A01N 65/22 424/59 |
| 2009/0081153 A1 | * | 3/2009 | Scott | A61K 31/045 424/78.31 |
| 2016/0030398 A1 | | 2/2016 | Dorgan | |
| 2026/0053746 A1 | | 2/2026 | Barrows | |

FOREIGN PATENT DOCUMENTS

| | | | | |
|---|---|---|---|---|
| CN | 105030732 A | 11/2015 | | |
| WO | 2011006079 | 1/2011 | | |
| WO | 2014053977 | 4/2014 | | |
| WO | 2014108573 | 7/2014 | | |
| WO | 2015038281 | 3/2015 | | |
| WO | WO-2016092569 A1 | * | 6/2016 | .......... A61K 31/192 |
| WO | WO-2018204764 A1 | * | 11/2018 | .......... C12N 15/113 |
| WO | 2019217448 | 11/2019 | | |

OTHER PUBLICATIONS

Google search for sulfamethazine (Year: 2024).*
Google search for cubic FD3M (Year: 2024).*
Google search for lecithin (Year: 2024).*
Suknuntha et al.; Characterization of muco- and bioadhesive properties of chitosan, PVP, and chitosan/PVP blends and release of amoxicillin from alginate beads coated with chitosan/PVP; Taylor & Francis; Drug Development and Industrial Pharmacy 37:4, 408-418, 2011 (Year: 2011).*
Tu et al.; Preparation, characterisation and evaluation of curcumin with piperine-loaded cubosome nanoparticles; Taylor & Francis; J Microencapsul, 2014; 31(6): 551-559 (Year: 2014).*
Akbar, et al., "Phytantriol based smart nano-carriers for drug delivery applications", European Journal of Pharmaceutical Sciences, 101:31-42 (2017).
Akhlaghi, et al., "Impact of preparation method and variables on the internal structure, morphology, and presence of liposomes in phytantriol-Pluronic@-127 cubosomes", Colloid and Surfaces B: Biointerfaces, 145:845-853 (2016).
Algharib, et al., "Nanoparticles for treatment of bovine *Staphylococcus aureus* mastitis", Drug Delivery, 27(1):292-308 (2019).
Aly, "Colorimetric determination of N—acetylcysteine through reduction of tetrazolium salts", Az J Pharm Sci, 37:83-90 (2008).
Ameen, et al., "Prevalence of antibiotic resistant pathogens in dairy cows in Egypt and potential biological control agents from plant endophytic actinobacteria", Saudi Journal of Biological Sciences, 26(7):1492-1498 (2019).
Araujo, et al., "Cloxacillin benzathine-loaded polymeric nanocapsules: Physicochemical characterization, cell uptake, and intramammary antimicrobial effect", Mater Sci Eng C: Mater Biol Appl, 104:110006 (2019).
Asli, et al., "Antibiofilm and antibacterial effects of specific chitosan molecules on *Staphylococcus aureus* isolates associated with bovine mastitis", PLoS One, 12(5):e0176988 (2017).

(Continued)

*Primary Examiner* — Robert A Wax
*Assistant Examiner* — John W Lippert, III
(74) *Attorney, Agent, or Firm* — Pabst Patent Group LLP

(57) ABSTRACT

Disclosed herein are compositions and methods of use thereof for the treatment of mastitis in dairy cattle. The compositions and methods can have improved effectiveness and duration of activity against mastitis-causing bacteria. In particular embodiments, the methods include treating mastitis infection by intramammary infusion of a disclosed composition.

22 Claims, 5 Drawing Sheets

(56)　　　　　　References Cited

OTHER PUBLICATIONS

Cao, et al., "Efficacy ofnisin in treatment of clinical mastitis in lactating dairy cows", J Dairy Sci, 90:3980-3985 (2007).

Chang, et al., "Binding of drugs to monoglyceride-based drug delivery systems", International Journal of Pharmaceutics, 147:135-142 (1997).

Chen, et al., "Protective effect of recombinant staphylococcal enterotoxin A entrapped in polylactic-co—glycolic acid microspheres against *Staphylococcus aureus* infection", Veterinary Research, 43(20):1-11 (2012).

Colladao-Gonzalez, et al., "Interaction between chitosan and mucin: fundamentals and applications", Biomimetics, 4(32):1-20 (2019).

Duttagupta, et al., "Chitosan: a propitious biopolymer for drug delivery", Current Drug Delivery, 12(4):369-381 (2015).

Eroshenko, et al., "N-acetylcysteine inhibits growih, adhesion and biofilm fomlation of gram-positive skin pathogens", Microbial Pathogenesis, 105:145-142 (2017).

Fonseca-Santos, et al., "In-situ gelling liquid crystal mucoadhesive vehicle for curcumin buccal administration and its potential application in the treatment of oral candidiasis", Journal of Biomedical Nanotechnology, 15: 1334-1344 (2019).

Gomes, et al., "Bovine mastitis disease/pathogenicity: evidence of the potential role of microbial biofilms", Pathogens and Disease, 74(3):1-7(2016).

Hozyen, et al., "Enhanced antibacterial activity of capped zinc oxide nanoparticles: A step tmvards the control of clinical bovine mastitis", Veterinary World, 12(8):1225-1223 (2019).

International Search Report for PCT application PCT/US2021/016165 dated Apr. 15, 2021.

Kamaruzzaman, et al., "Bactericidal and anti-biofilm effects of polyhexamethylene biguanide in models of intracellular and biofilm of *Staphylococcus aureus* isolated from bovine mastitis", Frontiers in Microbiology, 8(1518):1-10 (2017).

Liu, et al., "A fanctional chitosan-based hydrogel as a wound dressing and drug delivery system in the treatment of wound healing", RCS Adv., 8:7533-7549 (2018).

McLain, "Final report on the safety assessment of phytantriol", International Journal of Toxicology, 26(Suppl.1):107-114 (2007).

Milak, et al., "Glycerol monooleate liquid crystalline phases used in drug delivery systems", International Journal of Pharmaceutics, 478(2):569-588 (2015).

Paudyal, et al., "Relationships among quarter milk leukocyte proportions and cow and quarter-level variables under different intramammary infection statuses", Transl Anim Sci., 2:231-240 (2018).

Peralta, et al., "Safety and efficacy of a mesenchymal stem cell intramammary therapy in dairy cows with experimentally induced *Staphylococcus aureus* clinical mastitis", Scientific Reports, 10(2843): 1-12 (2020).

Pisano, et al., "Liquid crystal delivery of ciprotloxacin to treat infection of the female reproductive tract", Biomedical Microdevices, 21(36):1-12 (2019).

Roy, et al., "Strategies for combating bacterial biofilms: A focus on anti-biofilm agents and their mechanisms of action", Virulence, 9(1): 522-524 (2018).

Saber, et al, "Targeting colorectal cancer cell metabolism through development of cisplatin and metfom1in non-cubosomes", MBC Cancer, 18(822):1-11 (2018).

Souza, et al., "Mucoadhesive system formed by liquid c1ystals for buccal administration of poly(hexamethylene biguanide) hydrochloride", Journal of Pharmaceutical Sciences, 103:3914-3923 (2014).

Suknuntha, et al., "Characterization of muco- and bioadhesive properties of chitosan, PVP, and chitosan/PVP blends and release of amoxicillin from alginate beads coated with chitosan/PVP", Drug development and industrial pharmacy, 37(4): 408-418 (2001).

Xu, et al., "Characterization of a Liquid Crystal System for Sustained Release of a Peptide BJVIS.-686117", AAPS Pharm Sci Tech, 19(1):348-357 (2018).

Zhou, et al., "Enhanced treatment effects of tilmicosin against *Staphylococcus aureus* covv mastitis by self-assembly sodium alginatechitosan nanogel", Pharmaceutics, 11(524):1-17 (2019).

Tran, N. et al., 'Non-lamellar lyotropic liquid crystalline nanoparticles enhance the antibacterial effects of rifampicin against *Staphylococcus aureus*', Journal of Colloid and Interface Science, vol. 519, pp. 107-118. (2018).

Meikle, T.G. et al., 'Preparation, Characterization, and Antimicrobial Activity of Cubosome Encapsulated Metal Nanocrystals', ACS Applied Materials & Interfaces, vol. 12, No. 6, pp. 6944-6954(2020).

Ganem-Quintanar, et al., "Monoolein: a review of the pharmaceutical applications", Drug Development and Industrial Pharmacy, vol. 26, No. 8, 2000, pp. 809-820.

Yang, et al., "Short communication: N-Acetylcysteine-mediated modulation of antibiotic susceptibility of bovine mastitis pathogens", Journal of Dairy Science, vol. 99, No. 6, 2016, pp. 4300-4302.

Aboud, et al., "Novel in situ gelling vaginal sponges of sildenafil citrate-based cubosomes for uterine targeting", Drug Deliv. vol. 25, No. 1, Jun. 5, 2018, pp. 1328-1339.

\* cited by examiner

COMPOSITIONS AND METHODS OF USE THEREOF FOR TREATMENT OF MASTITIS

CROSS REFERENCE TO RELATED APPLICATION

This application is a National Phase application under U.S.C. § 371 of PCT/US2021/016165, filed Feb. 3, 2020, which claims the benefit of and priority to U.S. Ser. No. 62/969,419, filed Feb. 3, 2020, which are specifically incorporated by reference herein in their entireties.

FIELD OF THE INVENTION

The technical field of the invention generally includes antiseptic formulations and methods of controlled release of antimicrobials, particularly antiseptics, for prevention and treatment of mastitis, particularly bovine mastitis.

BACKGROUND OF THE INVENTION

Dairy farming is an important contribution to food supply worldwide. Although the reliable production of safe and wholesome milk is commonly viewed as proven and secure, this is the result of constant attention to the health of dairy cattle and insurance that milk from infected cows is discarded. Despite knowledge of the best practices for control, mastitis is a pervasive problem and the most common and costly disease in the dairy industry. The economic loss due to mastitis in the United States alone is estimated to be about 2 billion dollars per year, about 70% due to decreased milk production. A discussion of the background on bovine mastitis is provided by Lopez, et. al in WO2014/053977, as referenced herein. Mastitis prevention with the use of good sanitation, antiseptic teat dips, vaccines, and optimal feed diets is extremely important. Another common and highly recommended practice is the intramammary infusion of an antibiotic via the teat canal of each quarter for each cow in the herd at the end of its lactation cycle, known as the "dry-off" period.

Nevertheless, cows still suffer from mastitis at a troublesome rate. Typically, about 20% of the herd will have a low-grade, sub-clinical infection that causes no outward signs of distress but reduces milk production and results in the shedding of white blood cells into the milk. If the co-called "somatic cell count" (SCC) exceeds a certain value, the milk cannot be sold and the cow contributing to excessive SCC test results of milk in the bulk tank must be separated from the herd until cured. The cure rate is very low because antibiotics infused into the mammary of a lactating cow get washed out during milking, which must be continued 2 to 3 times each day. Typically, at least a third of cows severely infected during lactation end up being "culled", meaning that they are prematurely sold for slaughter. Culling is not profitable and represents a significant cost of dairy farming.

Compositions for treating mastitis have been investigated. An advantage to using an antiseptic rather than an antibiotic is the fear that development of antibiotic resistance could result in important antibiotics becoming ineffective. Moreover, the detectable presence of antibiotic residues in milk makes the milk unsalable.

Due to increased public awareness of the overuse of antibiotics in the livestock industry, naturally occurring antimicrobial substances have been investigated for use in treating mastitis. However, none so far have enough proven efficacy to displace the use of commercially available antibiotics. Thus, antibiotics continue to be the preferred therapeutic agent for intramammary infusion to treat mastitis in lactating cows.

Although antibiotics and antiseptics both kill bacteria, antibiotics have the advantage of being far less harmful to tissue if administered at high concentration or for a prolonged period of time. Antiseptics, on the other hand, have a broader spectrum of killing microorganisms, but at high concentration can destroy milk-producing tissue.

In the United States, almost all approved intramammary antibiotics are labeled for treatment of Streptococci and Staphylococci, and there are no approved products for treatment of mastitis caused by *Klebsiella* or many other pathogens that cause clinical mastitis. Only two antimicrobial classes are represented among commercially available products that are approved by the U.S. Food and Drug Administration (FDA). Those classes are β-lactams (amoxicillin, ceftiofur, cephapirin, cloxicillin, hetacillin, and penicillin) and a lincosamide (pirlimyein). While several products have been withdrawn from the U.S. market, no new intramammary antibiotics for lactating cows have been approved since 2006.

In addition to the problem of antibiotics being milked-out, mastitis treatment is made difficult by the fact that tissue damage resulting from prolonged sub-clinical infection facilitates the formation of chronically inflamed abscesses where bacteria become entrenched. Moreover, the bacteria are further ensconced within bacterial biofilms that insulate them from natural defense mechanisms and administered therapeutics.

There remains a need for convenient and economical compositions and methods of treating mastitis, particular mastitis in cows and/or goats, that are safe and effective.

Thus, it is an object of the invention to provide compositions and methods of use thereof for the treatment of mastitis.

It is another object of the invention to adapt antimicrobials, particularly antiseptics that previously have been deemed harmful, for safe use in the treatment of mastitis.

It is another object of the invention to reduce the amount, and/or frequency of use, of antibiotics in the treatment of mastitis, and thus preferably reduce overuse, ineffectiveness, and potential emergence of antibiotic resistant strains of mastitis-causing bacteria.

SUMMARY OF THE INVENTION

Compositions and methods for the treatment of mastitis in animals, particularly dairy animals, including but not limited to, cows and goats, are provided. The compositions typically include an emulsion of a liquid crystal-forming substance and one or more antimicrobial substances, anti-biofilm substances, or combination thereof, alone or optionally in further combination with a mucoadhesive substance. In some embodiments, a single substance has one or more of antimicrobial, anti-biofilm, and mucoadhesive activities. In some embodiments, liquid crystals form nanoparticles. Typically, the drug-releasing particles are capable of being "taken-up" by infected cells.

Exemplary liquid crystal-forming substances include, but are not limited to, monoolein, phosphatidyl choline, and phytantriol.

Exemplary antimicrobial substances include, but are not limited to, polyhexamethylene biguanide hydrochloride ("PHMB"), N-acetyl-L-cysteine ("NAC"), polyaminopropyl biguanide, chlorhexidine, benzalkonium chloride, stearalkonium chloride, amoxicillin, ceftiofur, cephapirin, cloxi-cillin, hetacillin, pirlimycin, and penicillin.

Exemplary anti-biofilm substances include, but are not limited to, PHMB, chitosan, NAC, 4-ethoxy benzoic acid, ethyl 4-ethoxybenzoate, methyl gallate, methyl paraben, 4-hydroxy-4-methyl-2-pentanone, adipic acid, phytol, phytol acetate, ellagic acid, esculetin, fisetin, reserpine, quercetin, linoleic acid, berberine, eugenol, and curcumin.

Exemplary mucoadhesive substances include, but are not limited to, polyethyleneimine ("PEI"), branched and dendrimeric forms of PEI, protamine, benzathine, spermidine, spermine, and chitosan In particular embodiments, the mucoadhesive is chitosan and the antimicrobial is PHMB.

In some embodiments, the chitosan is dissolved in an aqueous solution of N-acetyl-L-cysteine.

Exemplary non-limiting formulations can be found in Tables 1, 2, 3, and 4.

Methods of treating animals, particularly cows and goats, most particularly dairy cows and goats, for mastitis are also provided. The methods can include infusing any of the disclosed compositions into the mammary gland, for example, via the teat canal.

The disclosed compositions and methods can be used to deliver an antimicrobial, such as an antiseptic having superior efficacy, that optionally creates a substantive coating on intramammary tissue, and has a prolonged duration of antimicrobial activity, especially during lactation to cows in need thereof.

DETAILED DESCRIPTION OF THE INVENTION

I. Definitions

Figures 1A, 1B, 1C, 1D:
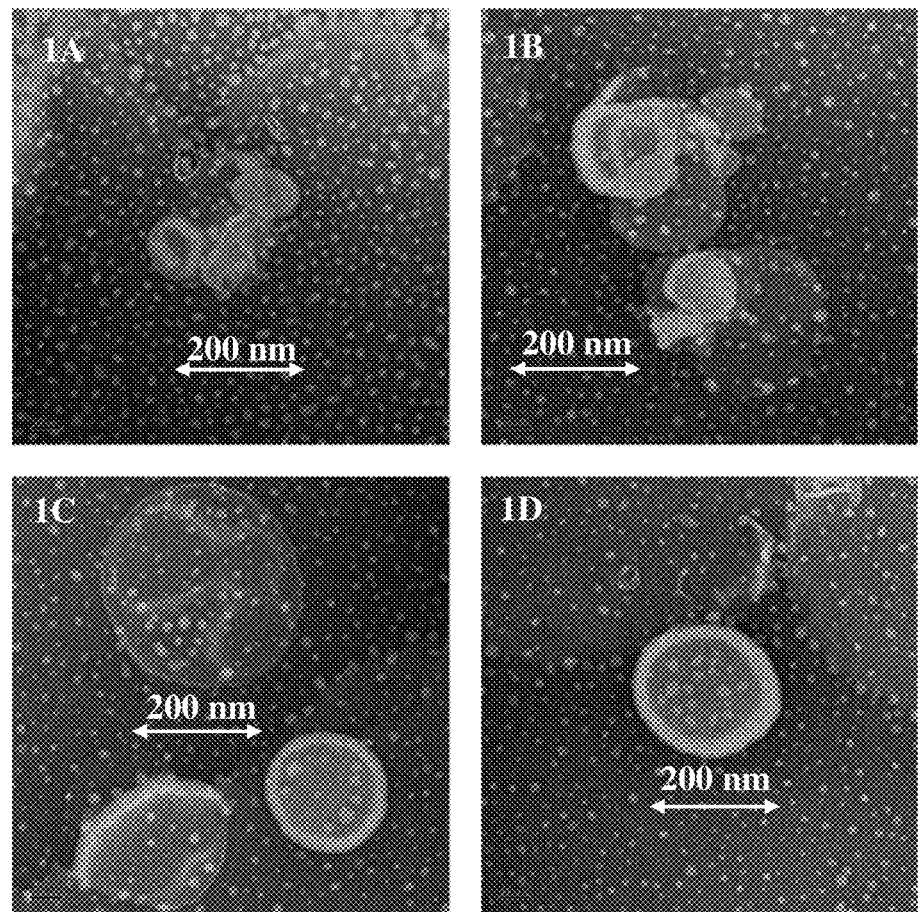
FIGS. 1A-1D are transmission electron micrographs of a sample of the emulsion of Example 1 after ultrasonic homogenization revealing the presence of nanoparticles in the size vicinity of 200 nanometers in diameter. The much smaller particles in the background are an artifact of the uranyl acetate (2% in water) negative staining procedure. Images were obtained in a JEOL JEM-1400 transmission electron microscope operated at 80 kV at the Robert P. Apkarian Integrated Electron Microscopy Core, Emory University, Atlanta, GA 30322.

As used herein, the term "antimicrobial" means an agent that kills microorganisms or stops their growth.

As used herein, the term "antibiotic" means an antimicrobial agent that kills bacteria or stops their growth.

As used herein, the term "antiseptic" means an antimicrobial substance that is traditionally or conventionally applied to living tissue/skin to reduce the possibility of infection, sepsis, or putrefaction. Antiseptics are generally distinguished from antibiotics by the latter's ability to safely destroy bacteria within the body, and from disinfectants, which destroy microorganisms found on non-living objects.

As used herein, the term "biofilm" means any syntrophic consortium of microorganisms stuck to each other and often also to a surface by means of a polymeric matrix synthesized by some of the microorganisms within the consortium. In some examples, the microorganisms are bacteria.

As used herein, the term "anti-biofilm" means a substance that reduces or prevents formation or maintenance of a biofilm. The anti-biofilm substance may or may not have antimicrobial (e.g., antibiotic or antiseptic) properties.

As used herein, the term "biodegradable" means that the material degrades or breaks down into its component subunits, or is enzymatically digested into smaller (e.g., non-polymeric) subunits.

As used herein, the terms "controlled release" and "sustained release" refer to release of a substance over an extended period of time in contrast to a bolus type administration in which the entire amount of the substance is made biologically available at one time.

As used herein, the term "nanoparticle" generally refers to a particle having a diameter from about 1 nm up to, but not including, about 1 micron, or from 100 nm to about 1 micron. The particles can have any shape. Nanoparticles having a spherical shape are generally referred to as "nanospheres". In certain embodiments, the particle size distribution may be uniform, e.g., within less than about a 20% standard deviation of the mean volume diameter, and in other embodiments, still more uniform, e.g., within about 10% of the median volume diameter.

As used herein, the terms "incorporated" and "encapsulated" refers to incorporating, formulating, or otherwise including an active agent into and/or onto a composition that allows for release, such as sustained release, of such agent in the desired application. The term "co-incorporation" or "co-encapsulation" refers to the incorporation of a therapeutic agent or other material and at least one other therapeutic agent or other material in a subject composition. For example, at least two actives can be encapsulated. In another example, at least three, at least four, at least five or more actives can be encapsulated.

As used herein, the term "treatment" refers to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "effective amount" refers to an amount of the composition (e.g., a therapeutic agent) that, when incorporated into and/or onto particles described herein, produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation. In some embodiments, the term "effective amount" refers to an amount of a therapeutic agent or prophylactic agent to reduce or diminish the symptoms of mastitis.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other forms the values may range in value either above or below the stated value in a range of approx. +/−5%; in other forms the values may range in value either above or below the stated value in a range of approx. +/−2%; in other forms the values may range in value either above or below the stated value in a range of approx. +/−1%. The preceding ranges are intended to be made clear by context, and no further limitation is implied.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a ligand is disclosed and discussed and a number of modifications that can be made to a number of molecules including the ligand are discussed, each and every combination and permutation of ligand and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D.

Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as herein can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Although the description of materials, compositions, components, steps, techniques, etc. can include numerous options and alternatives, this should not be construed as, and is not an admission that, such options and alternatives are equivalent to each other or, in particular, are obvious alternatives.

II. Compositions

Compositions typically including liquid crystals for the controlled release of an antimicrobial substance, and uses thereof for the treatment of mastitis are provided. The compositions and methods draw upon the technology of liquid crystals for the controlled release of drugs and the effectiveness of antimicrobials, particularly antisepties such as PHMB, against microorganisms that cause bovine mastitis. The compositions typically include liquid crystals including an antimicrobial substance and optionally an antibiofilm substance and/or a mucoadhesive.

Methods of using these compositions to treat infected cows are believed to improve recovery from mastitis. For example, in some embodiments, infected cows treated according to the disclosed methods recover from mastitis more quickly.

Also provided are processes for producing mastitis treatment formulations that are suitable for use on dairy cattle and readily administered by intramammary infusion, a procedure widely utilized and requiring no new equipment or training on the part of the dairy farmer or veterinarian.

A. Liquid Crystals

The compositions typically include liquid crystals, e.g., liquid crystal particles that are used for delivery, and controlled release of, an antimicrobial effective to treat mastitis.

For example, in some embodiments, the composition includes an aqueous emulsion of liquid-crystal particles wherein the particles include a lipid phase and an aqueous phase, wherein the aqueous phase contains a dissolved antimicrobial and/or anti-biofilm substance (e.g., an antiseptic substance, such as PHMB). The emulsion may be formed by mixing a liquid crystal-forming lipid and an appropriate surfactant with the aqueous solution of antiseptic under suitable conditions of temperature and agitation, such as with the use of an ultrasonic homogenizer. The emulsion can be packaged in standard, unit-dose intramammary syringes, commonly referred to as "tubes". Terminal sterilization of the filled tubes is not necessary because the antiseptic ingredient acts as a preservative.

The phenomenon of liquid crystal formation by certain types of amphiphilic substances is known in the art. For example, the liquid crystal-forming properties of the monoglyceryl ester of oleic acid (also known as "monoolein") have been investigated and reported in the scientific literature.

In some embodiments, the liquid crystals are formed from monoolein. Monoolein is commercially available in high purity from several suppliers, primarily BASF (Ludwigshafen, Germany) under the brand name of Monomuls® 90-O 18, and is used in liquid soaps, shower/bath formulas, hair colors, and skin care products.

Another equally well-characterized, liquid crystal-forming lipid is phytantriol, chemically named 3,7,11,15-tetramethyl-1,2,3-hexadecanetriol. Phytantriol is an ingredient in hair care products and is available from Koninklijke DSM N.V. (Royal DSM, commonly known as DSM), a Dutch multi-national company.

Like monoolein, phytantriol has a hydrophilic head group connected to a long, hydrophobic hydrocarbon chain, but unlike monoolein the hydrophilic and hydrophobic moieties cannot be separated by hydrolysis and thus phytantriol represents a hydrolytically stable alternative to monoolein. Thus, in some embodiments, the liquid crystals are formed from phytantriol.

Another liquid crystal forming substance is phosphatidyl choline, which has been studied for use in drug delivery as discussed in a publication by Xu, et al. (2018).

The compositions are typically formulated for controlled release. The concept of "controlled release" refers to a means by which a relatively large single dose of drug that might otherwise be toxic can be administered, typically by injection or orally, such that only a small amount of the drug becomes bioavailable per unit of time. A controlled-release dosage form, for example LUPRON DEPOT® (leuprolide acetate microsphere-encapsulated in a bioabsorbable polymer, AbbVie Inc. North Chicago, Illinois, U.S.A.), in a single injection can provide a constant blood level of drug for 30 days that could otherwise only be achieved with daily injections. Antibiotic cloxacillin benzathine (CLOXB) loaded into poly-ε-caprolactone (PCL) nanocapsules is described in Araujo R S, et al., (2019), as referenced herein. Some of these particles apparently were small enough to be internalized into mammalian cells in vitro. Internalization of bacteria into mammary epithelial cells is a known phenomenon that contributes to the persistence and recalcitrance of mastitis infections.

Procedures for making surfactant-stabilized emulsions of phytantriol in the form of liquid crystal "cubosomes" have been described by Akhlaghi S P, et al. (2016), as referenced herein. Monoolein, like phytantriol, also forms cubosome nanoparticles upon emulsification in the presence of a surfactant as described by Saber M M, et al. (2018), referenced herein. These types of emulsions are highly preferred for use in the disclosed compositions.

Compositions including monoolein and PHMB or ciprofloxacin are described in Souza, et al., 2014 and Pisano, et al., 2019, for their potential applications in the fields of dentistry and gynecology, respectively. In some embodiments, the disclosed methods utilize the same, similar, or different formulations to those in (Souza, et al., 2014) and (Pisano, et al., 2019).

Thus, in some embodiments the liquid crystals are formed of monoolein, phosphatidyl choline, or phytantriol. In some embodiments, the particles are nanoparticles or cubosomes.

In other embodiments, the liquid crystal structures include lamellar structures and/or mixtures of lamellar structures with cubic and hexagonal particles.

Each such nanoparticle typically contains both aqueous and lipid phases that are bicontinuous and interpenetrating, but non-communicating. This means that each such particle can serve to deliver a small dose of water-soluble material in a hydrophobic package. Moreover, particles of this size, only slightly larger than the size of viruses, can stick to tissue and penetrate mammalian cells by electrostatic forces and hydrophobic interactions In particular embodiments, the compositions and methods utilize liquid-crystal forming substances such as monoolein, phosphatidyl choline, and phytantriol to form small particles (known as "cubosomes") that are in the size range of e.g., 50-500 nanometers, or 100-400 nanometers, or 100-300 nanometers, or 240-375 nanometers.

In order to achieve a stable suspension of cubosomes and/or related nanoparticles it is typically desirable to add a surfactant to the formulation during particle formation. Suitable surfactants include, but are not limited to, block copolymers of poly(ethylene oxide) and poly(propylene oxide), for example Pluronic® F127 and other such non-ionic surfactants.

Despite the importance placed upon ultrasonic homogenization in descriptions of the preparation of liquid crystal emulsions, it was surprisingly discovered that use of an ultrasonic homogenizer is not critically required to prepare the disclosed compositions. As evidenced in the experiments of Example 3, the water soluble anti-biofilm ingredient N-acetyl-L-cysteine was prevented from rapid water removal from the emulsion whether or not the emulsion was subjected to ultrasonic treatment. Thus, mechanical homogenization is an acceptable alternative to ultrasonic homogenization as a method of forming the liquid crystal emulsions of the disclosed formulations. A preferred method of mechanical emulsification is the use of a rotor-stator device. Such devices are commercially available and as exemplified by the Omni Tissue Homogenizer (Omni International, Kennesaw, GA 20144).

B. Antimicrobial and Anti-Biofilm Substances

The compositions typically include one or more antimicrobial and/or anti-biofilm substances incorporated into or otherwise associated with the liquid crystals, e.g., liquid crystal particles. The antimicrobial can have antibiotic qualities, antiseptic qualities, or a combination thereof. Anti-biofilm substances typically reduce or prevent formation or maintenance of biofilm. In some embodiments, a single substance has both antimicrobial and anti-biofilm properties. Exemplary antimicrobial and anti-biofilm substances are discussed below.

In some embodiments, at least one of the substances is polyhexamethylene biguanide hydrochloride ("PHMB"). PHMB is a disinfectant used in swimming pools, hot tubs, and contact lens solutions and is commercially available as a 20% aqueous solution from Lonza (Basel, Switzerland) under the brand name VANTOCIL®. PHMB is also the active ingredient in an anti-infection wound care dressing (Organogenesis, Cambridge, MA, USA) under the brand name PURAPLY® AM. PHMB hydrochloride in solid form can be purchased from Cayman Chemical Co. (Ann Arbor, MI, USA).

A study on biofilm-forming bacteria associated with mastitis infections (Kamaruzzaman, et al. (2017)) indicated that PHMB may be an effective antiseptic for treatment of mastitis. However, due to its highly water soluble nature, administration of PHMB alone is believed to be insufficient to provide meaningful, lasting benefit if simply instilled into a lactating cow. Furthermore, in the case of PHMB, in vitro studies have shown that the minimum concentration to kill bacteria is about one milligram per liter whereas the minimum concentration to kill epithelial cells is about milligrams per liter. Accordingly, unlike an antibiotic, using conventional strategies, an antiseptic cannot be administered in high dose as a strategy for providing a long-lasting residue that prevents or stops the growth of bacteria within the mammary gland. Moreover, as mentioned previously, both antibiotics and antiseptics as currently formulated are equally susceptible to being rinsed out of the mammary gland during milking. Using liquid crystals to deliver antiseptics such as PHMB as disclosed herein addresses these problems.

An antiseptic similar to PHMB, namely chlorhexidine gluconate ("CHG"), has been used in some teat-dip products, but not for intramammary infusion. In fact, CHG is cytotoxic to cells within the mammary gland and in relatively high concentration can be used to destroy the milk producing capacity of a severely infected quarter if other quarters are not infected and continuing to produce salable milk. This is an alternative to culling a cow that has only one infected quarter. The cytotoxicity of PHMB, generally considered to be less than CHG, may be reduced further by sequestering it within liquid crystal structures from which it only slowly emerges. CHG also could be administered in this way for safe antiseptic use in the case where healing instead of destruction of milk-producing tissue is desired. Thus, in some embodiments, at least one of the substances of the composition is CHG.

Other substances are also contemplated for use alone or in combination with PHMB and/or CHG in the disclosed liquid crystal formulations.

For example, other compounds having useful antimicrobial properties include, but are not limited to, polyaminopropyl biguanide, benzalkonium chloride, stearalkonium chloride, and N-acetyl-L-cysteine, chlorhexidine, amoxicillin, ceftiofur, cephapirin, cloxicillin, hetacillin, pirlimycin, and penicillin. Any water-soluble substance or lipid-soluble substance including essentially all known antibiotics, including but not limited to those discussed herein, likewise may be beneficially administered.

Bacteria that produce biofilm as a mechanism for self-preservation and colony-formation are some of the most difficult to eliminate from infected tissue. Accordingly, much research has been devoted to the goal of depriving bacteria of this advantage, both in preventing its formation and in dispersing it once formed. A number of substances of natural origin, such as chitosan have both anti-biofilm and antimicrobial activity and may be formulated for treatment of mastitis as disclosed herein, but may be less potent than PHMB.

Other substances seem only effective against biofilm and have no antimicrobial activity, but could be useful in reducing the amount of antibiotic required to cure a biofilm-based infection. One such family of substances is obtained from extracts of the gesho plant as disclosed in WO 2019/217448, referenced herein, which include 4-ethoxy benzoic acid, ethyl 4-ethoxybenzoate, methyl gallate, methyl paraben, 4-hydroxy-4-methyl-2-pentanone, adipic acid, phytol, and/or phytol acetate.

An especially preferred anti-biofilm substance is N-acetyl-L-cysteine as discussed in the publication by Eroshenko, et al. (2017), also referenced herein. Other anti-biofilm agents include ellagic acid, esculetin, fisetin, reserpine, quercetin, linoleic acid, berberine, eugenol, and curcumin, see, e.g., Roy, et al. (2018).

C. Mucoadhesive Substances

In some embodiments, the formulations are mucoadhesive. The attribute of being "mucoadhesive", provides a means to increase adhesion of the antiseptic-releasing liquid crystal formulation to intramammary tissues despite concomitant lactation and milking. In some embodiments, the antimicrobial and/or anti-biofilm substance is also a mucoadhesive substance. In some embodiments, the formulation optionally further includes one or more separate mucoadhesive substances.

Mucoadhesive drug delivery formulations generally contain water soluble polymers that are polyelectrolytes, either positively or negatively charged. In some embodiments of the disclosed formulations, one or more polyanionic substances such as polyacrylic acid, hyaluronic acid, carboxymethyl cellulose, alginic acid, or the like are absent from the formulation or otherwise avoided because PHMB, being polycationic may be neutralized and precipitated by these materials. In fact, the mechanism of biocidal activity of PHMB is generally believed to be its ability to bind with the carboxylic acid functionality of bacterial membranes and biofilm molecules.

Examples of suitable mucoadhesive substances include, but are not limited to, polycationic polymers and multifunctional amines. Such substances include, for example, polyethyleneimine ("PEI"), branched and dendrimeric forms of PEI, protamine, benzathine, spermidine, spermine, chitosan, and related compounds and polymers Thus, some embodiments provide enhanced mucoadhesive potency of a formulation including an antiseptic and monoolein, phosphatidyl choline, or phytantriol by means of being further modified by addition of a polycationic polymer or multifunctional amine such as polyethyleneimine ("PEI"), branched and dendrimeric forms of PEI, protamine, benzathine, spermidine, spermine, chitosan, or a related compound or polymer.

Chitosan is especially preferred as a mucoadhesive because of its biocompatibility, high molecular weight, and high density of amine groups. Chitosan having a molecular weight of about 2.6 kDa has also been shown to possess anti-biofilm and antibacterial activity (see, e.g., Asli, et al. (2017), referenced herein).

Chitosan, however, is not water soluble and typically must be dissolved under acidic conditions, such as in dilute acetic acid. An especially preferred form of chitosan for use in the disclosed compositions and methods is chitosan dissolved in aqueous N-acetyl-L-cysteine ("NAC"), a sulfur-containing amino acid derivative having anti-inflammatory and anti-biofilm potency. In preferred embodiments, the activities of PHMB and NAC are facilitated by combining chitosan/NAC with PHMB/monoolein, phosphatidyl choline, or phytantriol. When PHMB and NAC are administered in combination, this combination may have an additive, or more than additive, antimicrobial or anti-biofilm activity relative to PHMB or NAC administered separately.

Regardless of its molecular weight, chitosan is a useful ingredient in many aspects of the disclosed compositions due to its proven healing efficacy and other useful attributes in the context of wound care products as reviewed in the publication by Liu, et al. (2018), referenced herein.

The advantage of including chitosan in the disclosed formulations is illustrated in Example 4, where the adhesion of the emulsions to fresh calf liver tissue as a surrogate for bovine mammary tissue was challenged by soaking in warm milk to simulate the intramammary environment present in lactating dairy cows. As exhibited in FIG. 4, the formulations containing chitosan revealed the presence of the NAC by colorimetric detection, which was less intense in the case of non-chitosan-containing formulations, and completely absent in liver treated with NAC dissolved in water.

D. Exemplary Formulations

Exemplary, non-limiting formulations are provided in Table 1 and 2 below, and Tables 3 and 4 in working Examples.

TABLE 1

| Ingredient | % composition (weight/volume) |
| --- | --- |
| Liquid crystal substance (e.g., monoolein) | 5-50 |
| Surfactant (e.g., non-ionic copolymer surfactant such as F-127) | 0.5-10 |
| Mucoadhesive (e.g., chitosan) | 0-10 |
| First Anti-biofilm and/or antimicrobial substance (e.g., PHMB) | 0.05-0.25 |
| Optional Second Anti-biofilm and/or antimicrobial substance (e.g., NAC) | 0-10 |
| Aqueous carrier (e.g., water) | Volume/volume (e.g., q.s. to 100%) |

TABLE 2

| Ingredient | % composition (weight/volume) |
| --- | --- |
| monoolein | 20-25 |
| F-127 | 0.5-3 |
| chitosan | 0.5-3 |
| PHMB | 0.05-0.2 |
| NAC | 0.5-3 |
| water | q.s. to 100% (volume/volume) |

II. Methods of Use

Methods of using the disclosed compositions for treating animals for mastitis are also provided. The methods typically include administering to an animal in need thereof an effective amount of a disclosed composition. In preferred embodiments, the animal is a cow, such as a dairy cow.

Goat milk also is an important commodity, especially outside of the USA. Mastitis in goats is frequently encountered and therefore also amenable to treatment using the disclosed compositions. Thus, in some embodiments, the animal is a goat.

Typically the composition is effective to reduce or prevent the colonization or spread of one or more mastitis-causing bacteria. In some embodiments, the composition eliminates the one or more bacteria from the mammary gland and/or other udder tissue. Mastitis-causing bacteria include *Pseudomonas aeruginosa, Staphylococcus aureus, Staphylococcus epidermidis, Streptococcus agalactiae, Streptococcus uberis, Brucella melitensis, Corynebacterium bovis, Mycoplasma* spp. (including *Mycoplasma bovis*), *Escherichia coli (E. coli), Klebsiella pneumoniae, Klebsiella oxytoca, Enterobacter aerogenes, Pasteurella* spp., *Trueperella pyogenes* (previously *Arcanobacterium pyogenes*), *Proteus* spp, *Prototheca zopfii* (achlorophyllic algae), and *Prototheca wickerhamii.*

The compositions can be administered directly or indirectly to the mammary gland and/or other udder tissue. The compositions can be administered by infusion. The compositions can be administered via the teat canal. In particularly preferred embodiments, the compositions are administered to the mammary gland by infusion via the teat canal.

In particular embodiments, the teat canal of one or more quarters of a cow is utilized to administer treatment, for example, at the end of a lactation cycle.

In some embodiments, the antimicrobial such as PHMB has anti-biofilm activity and is administered in an effective amount to reduce or prevent biofilm formation or maintenance in vivo.

The minimum inhibitory concentration ("MIC") of PHMB required to kill bacteria in vitro has been reported as 1 mg per liter (0.01%) and the cytotoxic limit ("CTL") of PHMB above which epithelial cells are killed in vitro has been reported as greater than 15 mg per liter (0.15%). A commercially available wound dressing that utilizes PHMB to kill bacteria is made by soaking the dressing in a 0.10% solution of PHMB.

It is believed that an intramammary infusion formulation including 0.10% PHMB would be effective at killing bacteria without damaging epithelial cells. However, such in vitro tests and calculations do not take into consideration the problem of such formulation being rinsed off the surfaces of infected tissue due to milking or the potential resistance to rinse-off facilitated by excipients that permit or enhance substantive coating of the tissue.

The disclosed liquid crystal formulations are believed to provide safe administration of a high dose of PHMB or other potent antiseptic that would otherwise be toxic. The liquid-crystal-facilitated controlled release of antiseptic optionally combined with mucoadhesive and/or anti-biofilm attributes are believed to facilitate a high level of efficacy with avoidance of cytotoxicity despite prolonged adherence of the formulation to the infected tissue.

Thus, the concentration of an antiseptic such as those utilized in the disclosed compositions and methods may be 0.10%, or may be higher, or may be lower.

The liquid crystal formulation sequesters some of the antiseptic. Thus, initially a minimally effective concentration from about 0.05% to 0.20% is administered and, as that concentration falls due to diffusion and dilution, additional antiseptic is leached out of the liquid crystals to replenish and restore an effective concentration. Since the formulation itself contains water, the concentration of the antiseptic partitioned between the liquid crystalline and aqueous phases of the formulation initially will be equal. In some embodiments, the concentration of PHMB is in the range of 0.05% to 0.25%.

Any of the disclosed methods may further include co-administration with a conventional therapy for mastitis including, but not limited, administration of one or more antibiotics. In some embodiments, the dose, frequency, or combination thereof, of antibiotic administered is lower than when administered in the absence of the disclosed compositions.

In some embodiments, the methods specifically exclude administration of an antibiotic absent a liquid crystal delivery system. In some embodiments, the methods specifically exclude administration of an antibiotic.

In some embodiments, infected cows treated according to the disclosed methods recover from mastitis more quickly than cows treated using conventional compositions and methods.

The disclosed compositions and methods can be further understood through the following numbered paragraphs.

1. A composition for the treatment of mastitis comprising an emulsion of a liquid crystal-forming substance and an antimicrobial substance.

2. The composition of paragraph 1 further comprising a mucoadhesive substance.

3. The composition of paragraphs 1 or 2 further comprising an anti-biofilm substance.

4. The composition of any one of paragraphs 1-3 wherein the liquid crystal-forming substance is monoolein.

5. The composition of any one of paragraphs 1-3 wherein the liquid crystal-forming substance is phytantriol.

6. The composition of any one of paragraphs 1-3 wherein the liquid crystal-forming substance is phosphatidyl choline.

7. The composition of any one of paragraphs 1-6 comprising nanoparticles formed of the liquid crystal-forming substance.

8. The composition of paragraph 7, wherein the nanoparticles comprise or consist of cubosomes.

9. The composition of any one of paragraphs 1-8 wherein the antimicrobial is selected from the group comprising PHMB, N-acetyl-L-cysteine, polyaminopropyl biguanide, chlorhexidine, benzalkonium chloride, stearalkonium chloride, amoxicillin, ceftiofur, cepbapirin, cloxicillin, hetacillin, pirlimycin, and penicillin.

10. The composition of any one of paragraphs 2-9 wherein the mucoadhesive is selected from the group comprising polyethyleneimine ("PEI"), branched and dendrimeric forms of PEI, protamine, benzathine, spermidine, spermine, and chitosan.

11. The composition of any one of paragraphs 2-10 wherein the mucoadhesive is chitosan and the antimicrobial is PHMB.

12. The composition of paragraphs 10 or 11 wherein chitosan is dissolved in an aqueous solution of N-acetyl-L-cysteine.

13. The composition of any one of paragraphs 3-12 wherein the anti-biofilm substance is comprised of one or more substances of the group comprising PHMB, chitosan, N-acetyl-L-cysteine, 4-ethoxy benzoic acid, ethyl 4-ethoxybenzoate, methyl gallate, methyl paraben, 4-hydroxy-4-methyl-2-pentanone, adipic acid, phytol, phytol acetate, ellagic acid, esculetin, fisetin, reserpine, quercetin, linoleic acid, berberine, eugenol, and curcumin.

14. The composition of any one of paragraphs 1-13, in formulation according to Table 1.

15. The composition of paragraph 13, in a formulation according to Table 2.

16. The composition of paragraph 15, in a formulation according to Tables 3 or 4.

17. The composition of any one of paragraphs 1-16, wherein the mastitis is cow mastitis (i.e., bovine mastitis) or goat mastitis.

18. A method of treating an animal for mastitis comprising administering the animal an effective amount of the composition of any one of paragraphs 1-17.

19. The method of paragraph 18, wherein the animal is a cow or a goat.

20. The method of paragraph 19, wherein the cow is a dairy cow.

21. The method of any one of paragraphs 18-20, wherein the composition is administered directly or indirectly to the mammary gland.

22. The method of any one of paragraphs 18-21, wherein the composition is administered by infusion.

23. The method of any one of paragraphs 18-22, wherein the composition is administered via the teat canal.

24. A method of treating mastitis in a dairy cow or goat by infusing a composition of any one of paragraphs 1-17 into the mammary gland of the cow or goat via the teat canal.

25. The method of any one of paragraphs 18-24, further comprising administering the animal an antibiotic.

The disclosed compositions are exemplified by the following examples, which are provided for illustration, and are non-limiting.

EXAMPLES

Example 1: Formulation of a Mastitis Treatment Composition Including Monoolein and N-Acetyl-L-Cysteine ("NAC")

Eighteen grams of monoolein (Monomuls® 90-018, BASF material no. 50294943) and 2.00 grams of Pluronic® F-127 (Sigma no. P2443, lot no. BCCB3537) were placed in a 50 mL tube and heated to 70° C. in a water bath until the solids melted and mixed to give a clear liquid.

A 2.0% solution of PHMB was prepared by placing 0.50 grams of PHMB (Carbosynth batch no. FP767041701) in a 50 mL tube and filling to the 25 mL mark with deionized water.

0.86 Grams of N-acetyl-L-cysteine (Sigma no. A7250, lot no. WXBD1851V) were placed in a 100 mL graduated cylinder and 5.0 mL of the above 2% PHMB solution added. Deionized water was added to obtain a final volume of 62 mL and the resultant solution was placed in a glass bottle.

About 5 mL of the above solution of NAC and PHMB were added to the above tube of molten monoolein/F-127 with stirring using a stainless steel rod, which rapidly caused the formation of a stiff coagulum. The tube was covered and allowed to rest overnight. The contents were then transferred to a 400 mL, glass beaker and the remaining NAC/PHMB solution was added in small portions with mixing between each addition to obtain first a stiff paste, and then ultimately a creamy, pourable liquid. Mixing and blending to eliminate lumps was accomplished with the use of a wooden tongue depressor by alternately smearing and scraping the mixture on the walls of the beaker.

The mixture was transferred to a 100 ml beaker containing a Teflon-clad spin bar and stirred on a magnetic mixing plate for about 15 minutes to obtain a smooth, uniform mixture.

The final composition was calculated to be composed of the ingredients listed below:

TABLE 3

| Ingredient | % composition (weight/volume) |
| --- | --- |
| water | 75.35 (volume/ volume) |
| monoolein | 21.18 |
| F-127 | 2.35 |
| NAC | 1.00 |
| PHMB | 0.12 |

This formulation was divided into two approximately equal portions; one portion was subjected to ultrasonic homogenization and the other portion was reserved as a non-ultrasonic homogenized control. Approximately 25 mL of the sample to be homogenized was place in a 50 ml beaker and a ⅛ inch diameter steel probe connected to a 600 watt Cole-Parmer CPX-600 model ultrasonic homogenizer was immersed into the liquid, which was continuously stirred with a Teflon-clad spin bar in the beaker on a magnetic mixing plate.

The ultrasonic homogenization consisted of 15 minutes of sonication pulses, each pulse being 1.5 seconds long followed by a 0.5 second pause to prevent excessive heating. A temperature probe connected to the homogenizer was placed in the liquid and set to a high limit of 30° C., which was not exceeded during ultrasonication.

The sample that was treated with the ultrasonic homogenizer had no discernable difference in appearance from the sample that was not subjected to ultrasonic homogenization except that it seemed to be slightly more fluid.

Example 2: Formulation of a Mastitis Treatment Composition Including Monoolein, Chitosan, and NAC Materials and Methods Two grams of chitosan (Spectrum Chemical no. C1569, lot no. 1HD1928) and 1.01 grams of N-acetyl-L-cysteine (Sigma no. A7250, lot no. WXBD1851V) were placed in a 50 mL conical tube, deionized water added to the 30 mL mark, and the viscous mixture stirred with a stainless steel rod. The tube was then covered with a threaded cap and allowed to rest at room temperature overnight to allow the contents to fully hydrate and dissolve.

Eighteen grams of monoolein (Monomuls® 90-018, BASF material no. 50294943) and 2.00 grams of Pluronic® F-127 (Sigma no. P2443, lot no. BCCB3537) were placed in a 50 mL tube and heated to 70° C. in a water bath until the solids melted and mixed to give a clear liquid.

A 2.0% solution of PHMB was prepared by placing 0.50 grams of PHMB (Carbosynth batch no. FP767041701) in a 50 mL tube and filling to the 25 mL mark with deionized water. Exactly 5.0 mL of this PHMB solution was added to the above chitosan/NAC solution and stirred to mix. About 5 mL of this solution of chitosan/NAC/PHMB was added to the above tube of molten monoolein/F-127 with stirring, which rapidly caused the formation of a stiff coagulum. The tube was covered and allowed to rest overnight. The contents were then transferred to a 400 mL glass beaker and the remaining chitosan/NAC/PHMB solution was added in small portions with mixing between each addition to obtain a stiff paste. Mixing and blending to eliminate lumps was accomplished with the use of a wooden tongue depressor by alternately smearing and scraping the mixture on the walls of the beaker. The resultant paste was thinned to a creamy, pourable consistency by continuing the mixing process with portion-wise addition of 35 mL of deionized water containing 1.0% NAC and 0.12% PHMB. The final composition was calculated to be comprised of the ingredients listed below:

TABLE 4

| Ingredient | % composition (weight/volume) |
| --- | --- |
| water | 73.17 (volume/volume) |
| monoolein | 21.20 |
| F-127 | 2.35 |
| chitosan | 1.81 |
| NAC | 1.33 |
| PHMB | 0.14 |

This formulation was divided into two approximately equal portions; one portion was subjected to ultrasonic homogenization and the other portion reserved as a non-ultrasonic homogenized control. A approximately 25 mL of the sample to be homogenized was place in a 50 mL beaker and a ⅛ inch diameter steel probe connected to a 600 watt Cole-Parmer CPX-600 model ultrasonic homogenizer was immersed into the liquid. The ultrasonic homogenization was performed exactly as described in Example 1.

Results

The sample that was treated with the ultrasonic homogenizer had no discernable difference in appearance from the sample that was not subjected to ultrasonic homogenization.

Example 3: Evaluation of the Migration of NAC from NAC-Containing Monoolein Emulsions with the Use of Paper Chromatography Materials and Methods Paper chromatography was utilized to evaluate the release of soluble NAC from the formulations of Examples 1 and 2 using a colorimetric reagent to develop the chromatograms as follows:

Three strips of chromatography paper were marked with pencil to indicate the "origin" and spotted with a small dot of each of the two samples. The third strip was spotted with a drop of aqueous NAC only. Each strip was suspended in a separate jar with deionized water just covering the bottom of the jar. The bottom edge of each paper strip was positioned to be immersed in water, which gradually migrated up the strip. After upward water migration wet approximately 6 to 8 cm of the paper, the "solvent front" was marked with pencil and the strips were allowed to dry completely.

Tetrazolium blue chloride (Sigma no. T4375, lot no. SHBM0991) was dissolved in denatured ethyl alcohol to obtain a 1% solution and transferred to a small spray bottle. The dry chromatography strips were placed in a chemical fume hood, sprayed with the tetrazolium solution, and allowed to dry again. An ammonia chamber was created by coving the bottom of a large glass canister with concentrated ammonium hydroxide and the chromatography paper strips were suspended just above the liquid with the canister covered until a purple color developed, indicating the presence of NAC.

Results

Figure 2A:
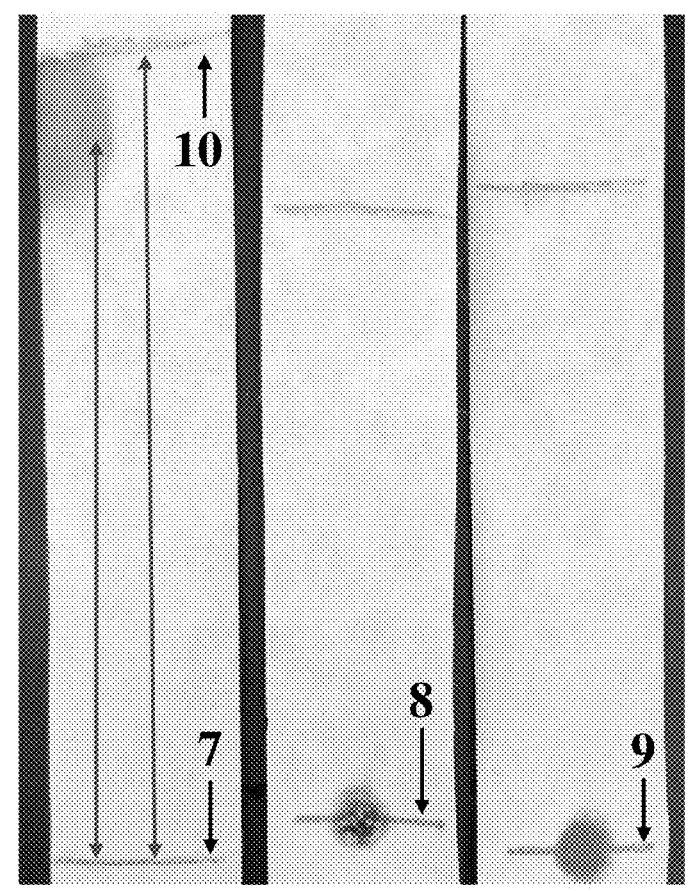
FIG. 2A is a photograph of the chromatograms of samples from Example 1 as described in Example 3. The strip on the left was spotted at the origin (7) with aqueous NAC only; the strip in the center was spotted at the origin (8) with the non-ultrasonicated monoolein emulsion sample of Example 1; and the strip on the right was spotted at the origin (9) with the ultrasonicated monoolein emulsion sample of Example 1. The double-headed arrows on the NAC only chromatogram show migration of the NAC upward almost to the solvent front (10), giving an Rf value of 0.91 (i.e., distance of NAC from the origin divided by the distance of the solvent front from the origin). In contrast, neither of the monoolein emulsion samples of Example 1 exhibited any NAC migration.
Figure 2B:
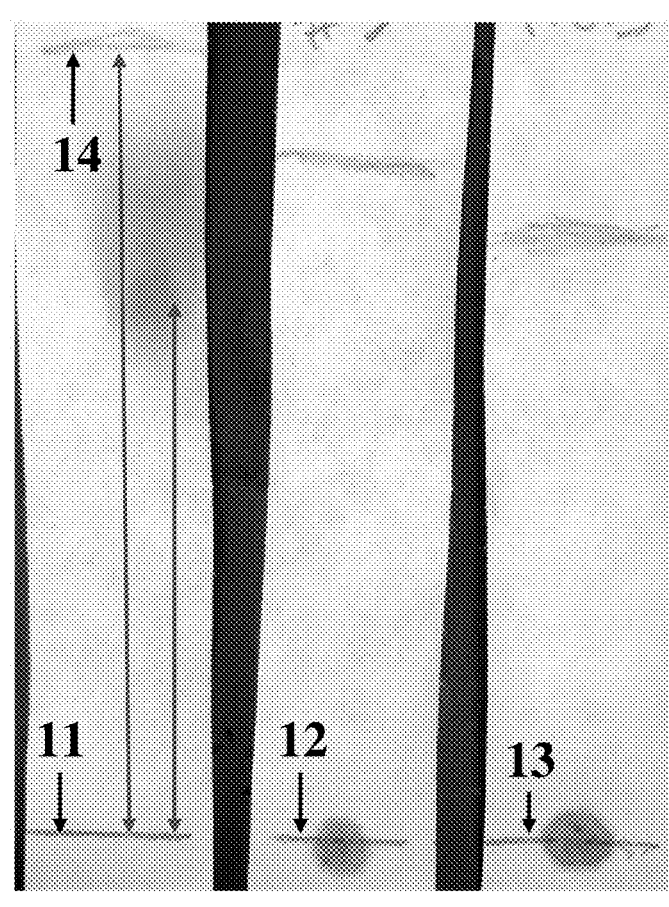
FIG. 2B is a photograph of the chromatograms of samples from Example 2 as described in Example 3. The strip on the left was spotted at the origin (11) with aqueous NAC only; the strip in the center was spotted at the origin (12) with the non-ultrasonicated monoolein emulsion sample of Example 2; and the strip on the right was spotted at the origin (13) with the ultrasonicated monoolein emulsion sample of Example 2. The double-headed arrows on the NAC only chromatogram show upward migration of the NAC toward the solvent front (14), giving an Rf value of 0.67. In contrast, neither of the monoolein emulsion samples of Example 2 exhibited any NAC migration.

As shown in FIGS. 2A and 2B, NAC deposited from an aqueous solution migrated from the origin and was carried by water up the strip of chromatography paper. In stark contrast, none of the monoolein emulsion samples from Examples 1 and 2 exhibited any migration of NAC, which as detected by purple color remained at the origin where originally deposited.

These results can be interpreted as evidence for the entrapment of NAC within the liquid crystal structures of the formulation created during emulsification. Release of NAC to allow its detection on the chromatograms was likely facilitated by the alcohol content of the tetrazolium spray that may have collapsed the liquid crystalline structures and released detectable NAC.

Figure 3A:
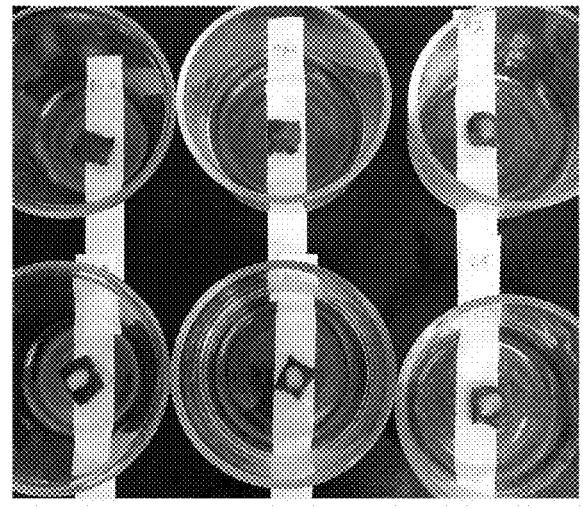
FIG. 3A is a photograph of a series of specimens of raw calf liver utilized as surrogate tissue to represent intramammary bovine tissue and treated with emulsions of Examples 1 and 2, including untreated liver as a blank control and liver treated an aqueous solution of NAC as a negative control.
Figure 3B:
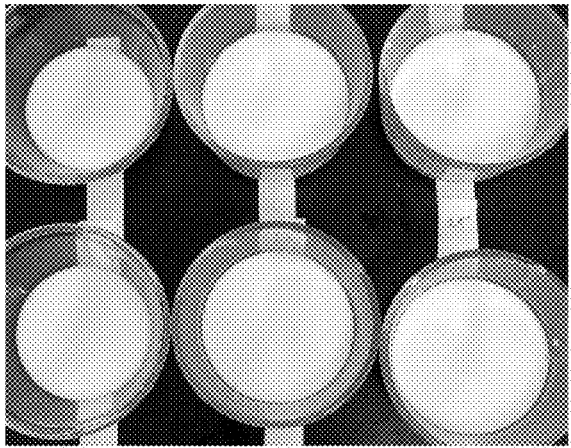
FIG. 3B is a photograph showing the dishes containing the liver specimens of FIG. 3A covered with warm whole milk to simulate intramammary conditions in lactating dairy cows.

Example 4: Evaluation of the Substantivity of NAC-Containing Monoolein Emulsions on Bovine Organ Tissue in the Presence of Milk Materials and Methods As a surrogate for bovine intramammary tissue, fresh calf liver was purchased frozen from a grocery store in the form of approximately 5 mm thick slices. Upon thawing to room temperature a slice of liver was cut into approximately 1×2 centimeter pieces and placed separately into each of 6 small glass dishes. One of the dishes of liver was left untreated as a blank control specimen and the others were treated with a few drops of the emulsions of Examples 1 and 2, both before and after ultrasonication. A sixth sample of liver was treated with a few drops of a 1% solution of NAC in deionized water as a negative control. As shown in FIG. 3B, the dishes were filled with whole milk warmed to 30° C. and left to soak for about 30 minutes. The milk was then decanted and replaced with deionized water and allowed to soak for a few minutes more before also being decanted. The liver specimens were lifted out of the dishes with forceps and placed treated-side up on paper towels. Strips of chromatography paper were then gently pressed onto the surface of each specimen and then sprayed with a solution to tetrazolium in ethanol, allowed to dry slightly, then peeled off the liver and the reverse side also sprayed with tetrazolium. The papers were allowed to dry completely and then suspended in a chamber of ammonia vapor to develop color to detect the presence of NAC.

Results

Figure 4:
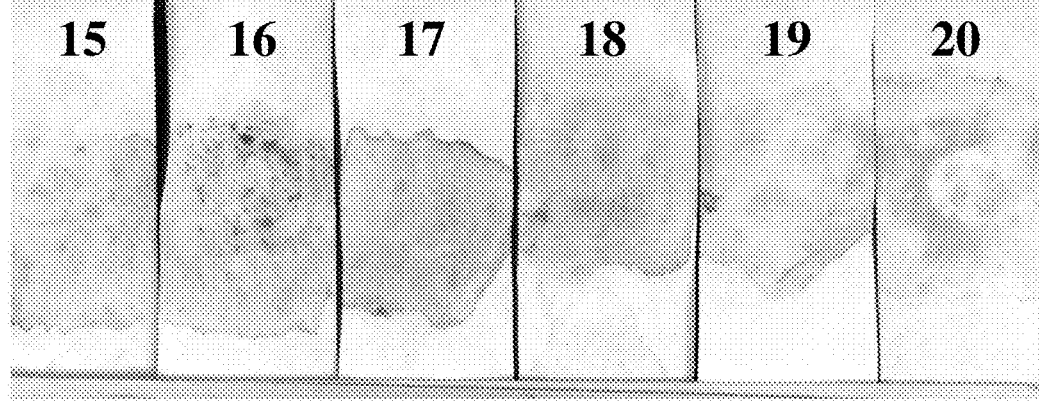
FIG. 4 is a photograph of chromatography paper strips recovered from the experiment depicted in FIGS. 3A-3B. The warm milk shown in FIG. 3B was poured off the liver specimens, which were then rinsed with deionized water. Chromatography paper strips were pressed onto the liver specimens, sprayed with tetrazolium solution, removed from the liver, sprayed again with tetrazolium, and placed in a chamber of ammonia vapor to develop violet color that would indicate the presence of NAC. The blank control of untreated liver (15) and the aqueous NAC treated liver (16) failed to show the presence of any violet color against the background of fluids transferred from the liver to the paper. Samples (17) and (18) are from Example 1 before and after ultrasonication, respectively, and samples (19) and (20) are from Example 2 before and after ultrasonication, respectively. Regions of detectable violet color indicating the presence of NAC were identified. The sample that appears to have the best retention of NAC on tissue after the milk soak test (20) appears to be the ultrasonicated monoolein emulsion containing chitosan.

As shown in FIG. 4, NAC was detectable by a faint violet color against the background of fluid stains transferred from the liver to the paper. Violet color was not detected in the blank or NAC control specimens, but was detected in all of the monoolein emulsions of the present invention. The most intensely detected color corresponded to the Example 2 ultrasonicated sample containing chitosan.

All references, including references cited therein and the teachings thereof are incorporated by reference herein in their entireties.

BIBLIOGRAPHY

Akbar S, Anwar A, Ayish A, Elliott J M, and Squires A M, "Phytantriol based smart nano-carriers for drug delivery applications", *European Journal of Pharmaceutical Sciences,* 101, 31 (2017).

Akhlaghi S P, Ribeiro I R, Boyd B J, and Loh W, "Impact of preparation method and variables on the internal structure, morphology, and presence of liposomes in phytantriol-Pluronic®-127 cubosomes", *Colloids and Surfaces B: Biointerfaces,* 145, 845 (2016).

Ameen F, et al., "Prevalence of antibiotic resistant pathogens in dairy cows in Egypt and potential biological control agents from plant endophytic actinobacteria", *Saudi Journal of Biological Sciences,* 26, 1492-1498 (2019).

Aly O M, "Colorimetric determination of N-acetylcysteine through reduction of tetrazolium salts", Az *J Pharm Sci,* 37, 83-90 (2008).

Araújo R S, et al., "Cloxacillin benzathine-loaded polymeric nanocapsules: Physicochemical characterization, cell uptake, and intramammary antimicrobial effect", *Mater Sci Eng C: Mater Biol Appl,* 104, 110006 (2019).

Asli A, et al., "Antibiofilm and antibacterial effects of specific chitosan molecules on *Staphylococcus aureus* isolates associated with bovine mastitis", *PLOS ONE,* 12:5 (2017).

Bradley C M, et al., "Assembly for sequentially delivering substances and associated methods", WO 2015/038281, Mar. 19, 2015.

Campbell M and Gilbert E, "Compositions and methods related to Rhamus *Prinoides* (Gesho) Extract for the Inhibition of Polymicrobial Biofilm formation", WO 2019/217448, Nov. 4, 2019.

Cao L T, Wu J Q, Xie F, Hu S H, and Mo Y, "Efficacy of nisin in treatment of clinical mastitis in lactating dairy cows", *J. Dairy Sci,* 90:3980 (2007)

Chang C and Bodmeier R, "Binding of drugs to monoglyceride-based drug delivery systems", *International Journal of Pharmaceutics,* 147, 135 (1997).

Chen L, et al., "Protective effect of recombinant staphylococcal enterotoxin A entrapped in polylactic-co-glycolic acid microspheres against *Staphylococcus aureus* infection", *Veterinary Research,* 43:20, 1-11 (2012).

Colladao-González M, et al., "Interaction between chitosan and mucin: fundamentals and applications", *Biomimetics,* 4, 32 (2019).

Damani N C, "Sustained release compositions for treating periodontal disease", U.S. Pat. No. 5,262,164, Nov. 16, 1993.

Dibyangana S, et al., "Chitosan: a propitious biopolymer for drug delivery", *Current Drug Delivery,* 12:4, 369 (2015).

Dorgan R J J, "Veterinary compositions for treating mastitis", US Patent Publication US2016/0030398, Feb. 4, 2016.

Eroshenko D, Polyudova T, and Korobov V, "N-acetylcysteine inhibits growth, adhesion and biofilm formation of gram-positive skin pathogens", *Microbial Pathogenesis,* 105, 145 (2017).

Fonseca-Santos B, Bonifacio B V, Baub T M, et al., "In-situ gelling liquid crystal mucoadhesive vehicle for curcumin buccal administration and its potential application in the treatment of oral candidiasis", *Journal of Biomedical Nanotechnology,* 15:1334 (2019).

Gomes F, Saavedra M J, and Henriques M, "Bovine mastitis disease/pathogenicity: evidence of the potential role of microbial biofilms". *Pathogens and Disease,* 74:3, 1-7 (2016).

Hozyen H F, et al., "Enhanced antibacterial activity of capped zinc oxide nanoparticles: A step towards the control of clinical bovine mastitis", *Veterinary World,* 12:8, 1225-1223 (2019).

Kamaruzzaman N F, Chong S Q Y, Edmondson-Brown K M, Ntow-Boahene W, Bardiau M, and Good L, "Bactericidal

19 and anti-biofilm effects of polyhexamethylene biguanide in models of intracellular and biofilm of *Staphylococcus aureus* isolated from bovine mastitis", *Frontiers in Microbiology*, 8, 15518 (2017).

Liu H, et al., "A functional chitosan-based hydrogel as a wound dressing and drug delivery system in the treatment of wound healing", *RCS Adv.*, 8, 7533 (2018).

Lopez C, Carrasco M, Gallardo P, Rademacher H, and Gomez G, "Natural antiseptic solution to be used as teat dip (dipping) during milking for prevention and control of mastitis", WO 2014/053977, Apr. 10, 2014.

MeLain V C, "Final report on the safety assessment of phytantriol", *International Journal of Toxicology*, 26 (Suppl. 1): 107-114 (2007).

Milak S and Zimmer A, "Glycerol monooleate liquid crystalline phases used in drug delivery systems", *International Journal of Pharmaceutics*. 478:2, 569 (2015).

Paudyal S, et al., "Relationships among quarter milk leukocyte proportions and cow and quarter-level variables under different intramammary infection statuses", *Transl Anim Sci*, 2, 231-240 (2018).

Peralta O A, et al., "Safety and efficacy of a mesenchymal stem cell intramammary therapy in dairy cows with experimentally induced *Staphylococcus aureus* clinical mastitis", *Scientific Reports*, 10, 2841 (2020).

Pisano S, et al., "Liquid crystal delivery of ciprofloxacin to treat infection of the female reproductive tract", *Biomedical Microdevices*, 21:36 (2019).

Roy R, et al., "Strategies for combating bacterial biofilms: A focus on anti-biofilm agents and their mechanisms of action", *Virulence*, 9 (1), 522 (2018).

Saber M M, et al., "Targeting colorectal cancer cell metabolism through development of cisplatin and metformin non-cubosomes", *MBC Cancer*, 18:822 (2018).

Souza C, Watanabe E, Borgheti-Cardoso L N, Fantini M C, and Lara M G, "Mucoadhesive system formed by liquid crystals for buccal administration of poly(hexamethylene biguanide) hydrochloride", *Journal of Pharmaceutical Sciences*, 103, 3914 (2014).

Zhou K, et al., "Enhanced treatment effects of tilmicosin against *Staphylococcus aureus* cow mastitis by self-assembly sodium alginate-chitosan nanogel", *Pharmaceutics*, 11, 524 (2019).

Xu Y, et al., "Characterization of a Liquid Crystal System for Sustained Release of a Peptide BMS-686117", *AAPS Pharm Sci Tech*, 19 (1), 348 (2018).

While the invention has been illustrated by a description of embodiments described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative examples shown and described. Accordingly, departures may be made from such details without departing from the spirit or scope of applicants' general inventive concept.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. An antimicrobial composition for the treatment of mastitis comprising an emulsion comprising cubosome nanoparticles formed of a liquid crystal-forming substance and an antimicrobial substance; and
wherein the cubosome nanoparticles have a size ranging from between 50-500 nanometers.

2. The composition of claim 1 further comprising a mucoadhesive substance.

3. The composition of claim 2 further comprising an anti-biofilm substance.

4. The composition of claim 3, wherein the liquid crystal-forming substance is monoolein.

5. The composition of claim 3, wherein the liquid crystal-forming substance is phytantriol.

6. The composition of claim 3, wherein the liquid crystal-forming substance is phosphatidyl choline.

7. The composition of claim 1, the composition further comprising a surfactant.

8. The composition of claim 1, wherein the composition comprises the antimicrobial substance.

9. The composition of claim 8, wherein the antimicrobial substance is selected from the group consisting of polyhexamethylene biguanide hydrochloride, N-acetyl-L-cysteine, polyaminopropyl biguanide, chlorhexidine, benzalkonium chloride, stearalkonium chloride, amoxicillin, ceftiofur, cephapirin, cloxicillin, hetacillin, pirlimycin, and penicillin.

10. The composition of claim 2, wherein the mucoadhesive substance is selected from the group consisting of polyethyleneimine ("PEI"), branched and dendrimeric forms of PEI, protamine, benzathine, spermidine, spermine, and chitosan.

11. The composition of claim 2, wherein the mucoadhesive substance is chitosan and the composition further comprises the antimicrobial substance that is polyhexamethylene biguanide hydrochloride.

12. The composition of claim 3, wherein the anti-biofilm substance is comprised of one or more substances of the group consisting of polyhexamethylene biguanide hydrochloride, chitosan, N-acetyl-L-cysteine, 4-ethoxy benzoic acid, ethyl 4-ethoxybenzoate, methyl gallate, methyl paraben, 4-hydroxy-4-methyl-2-pentanone, adipic acid, phytol, phytol acetate, ellagic acid, esculetin, fisetin, reserpine, quercetin, linoleic acid, berberine, eugenol, and curcumin.

13. The composition of claim 7, wherein the surfactant is a non-ionic copolymer surfactant.

14. The composition of claim 1, wherein the mastitis is cow mastitis or goat mastitis.

15. A method of treating an animal for mastitis comprising administering to the animal an effective amount of the composition of claim 1.

16. The method of claim 15, wherein the animal is a cow or a goat.

17. The method of claim 16, wherein the cow is a dairy cow.

18. The method of claim 15, wherein the composition is administered directly or indirectly to the mammary gland.

19. The method of claim 15, wherein the composition is administered by infusion.

20. The method of claim 15, wherein the composition is administered via the teat canal.

21. A method of treating mastitis in a dairy cow or goat by infusing the composition of claim 1 into the mammary gland of the cow or goat via the teat canal.

22. The method of claim 21, further comprising administering to the animal an antibiotic.

* * * * *